United States Patent [19]

Ueda

[11] Patent Number: 5,012,111
[45] Date of Patent: Apr. 30, 1991

[54] ION BEAM IRRADIATION APPARATUS

[75] Inventor: Kazuhiro Ueda, Amagasaki, Japan

[73] Assignee: Mitsubishi Denki Kabushiki Kaisha, Tokyo, Japan

[21] Appl. No.: 366,539

[22] Filed: Jun. 15, 1989

[30] Foreign Application Priority Data

Jun. 21, 1988 [JP] Japan .................................. 63-154108

[51] Int. Cl.$^5$ ........................................... G21K 1/043
[52] U.S. Cl. .............................. 250/492.3; 250/492.1; 250/492.2
[58] Field of Search ............. 250/492.3, 492.1, 492.21, 250/492.2; 363/58, 56

[56] References Cited

U.S. PATENT DOCUMENTS

| | | | |
|---|---|---|---|
| 3,965,434 | 6/1976 | Helgesson | 250/492.3 |
| 4,110,623 | 8/1978 | Azam et al. | 250/492.3 |
| 4,283,631 | 8/1981 | Turner | 250/492.21 |
| 4,410,926 | 10/1983 | Hafner et al. | 363/58 |
| 4,593,200 | 6/1986 | McGuire | 250/492.21 |
| 4,670,832 | 6/1987 | Park | 363/56 |
| 4,814,244 | 3/1989 | Koguchi et al. | 250/492.3 |
| 4,835,399 | 5/1989 | Hosaka et al. | 250/492.2 |
| 4,851,693 | 7/1989 | Fisher | 250/492.3 |

FOREIGN PATENT DOCUMENTS 2953877  4/1981  Fed. Rep. of Germany .

OTHER PUBLICATIONS

Article Entitled "A Kicker Magnet for Sweeping Ion Beams From a Medical Cyclotron", revised Dec. 30, 1986.
Article Entitled "Industrial Electron Accelerators and Applications", pp. 193–201, Published in Moscow 1986.
Wobbler Facility for Biomedical Experiments at the Bevalac, Timothy R. Renner and William T. Chu Med. Phys. 14 (5) Sep./Oct. 1987.
Wobbler Facility for Biomedical Experiments at the Bevalac W. T. Chu, S. B. Curtis, J. Llacer, T. R. Renner, and R. W. Sorensen IEEE Transactions on Nuclear Science, vol. NS-32, No. 5, Oct. 1985.

Primary Examiner—Jack I. Berman
Assistant Examiner—Kiet T. Nguyen

[57] ABSTRACT

An ion-beam irradiation apparatus is provided which has x- and y-deflection magnets to wobble an ion beam for uniformly irradiating a field exceeding the beam diameter in size. An exciting current is supplied to the x- and y-deflection magnets independently, and the exciting current inlcudes both an ac component and a dc bias component. Suitable control of these components enables the irradiated field to be varied in shape and location. In particular, racetrack-shaped fields can be irradiated by adding dc components to triangular ac components. When used in cancer radio therapy, this apparatus enables the irradiated field to be moved quickly from one location to another, and to be matched with the shape of the tumor. Benefits of this apparatus include short treatment times and efficient use of the ion beam, so that substantially all of the ion beams may be delivered to the target.

8 Claims, 7 Drawing Sheets

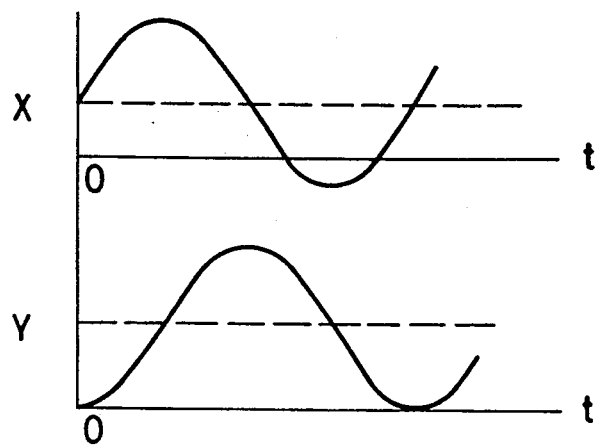
FIG.7
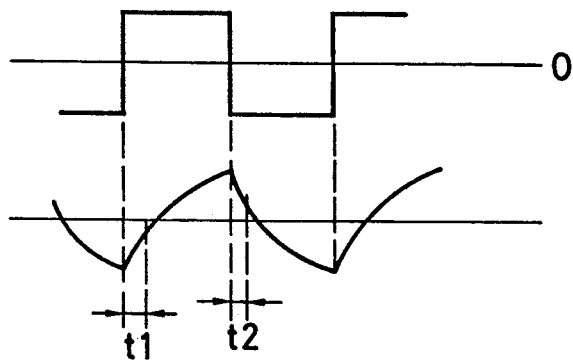
FIG.9A
FIG.9B
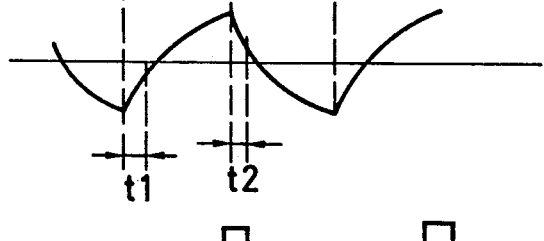
FIG.9C
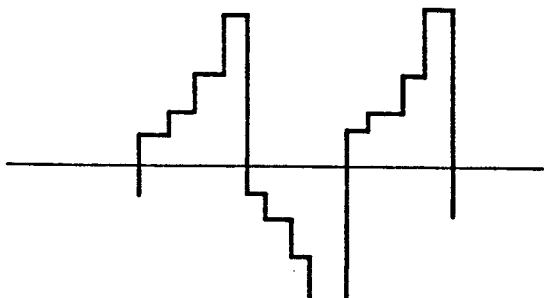
FIG.9D
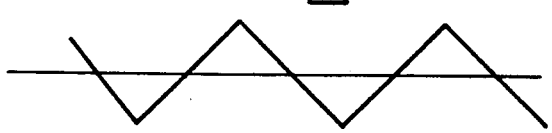
FIG.9E
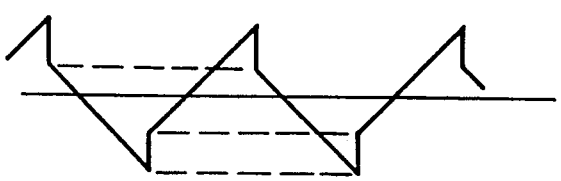

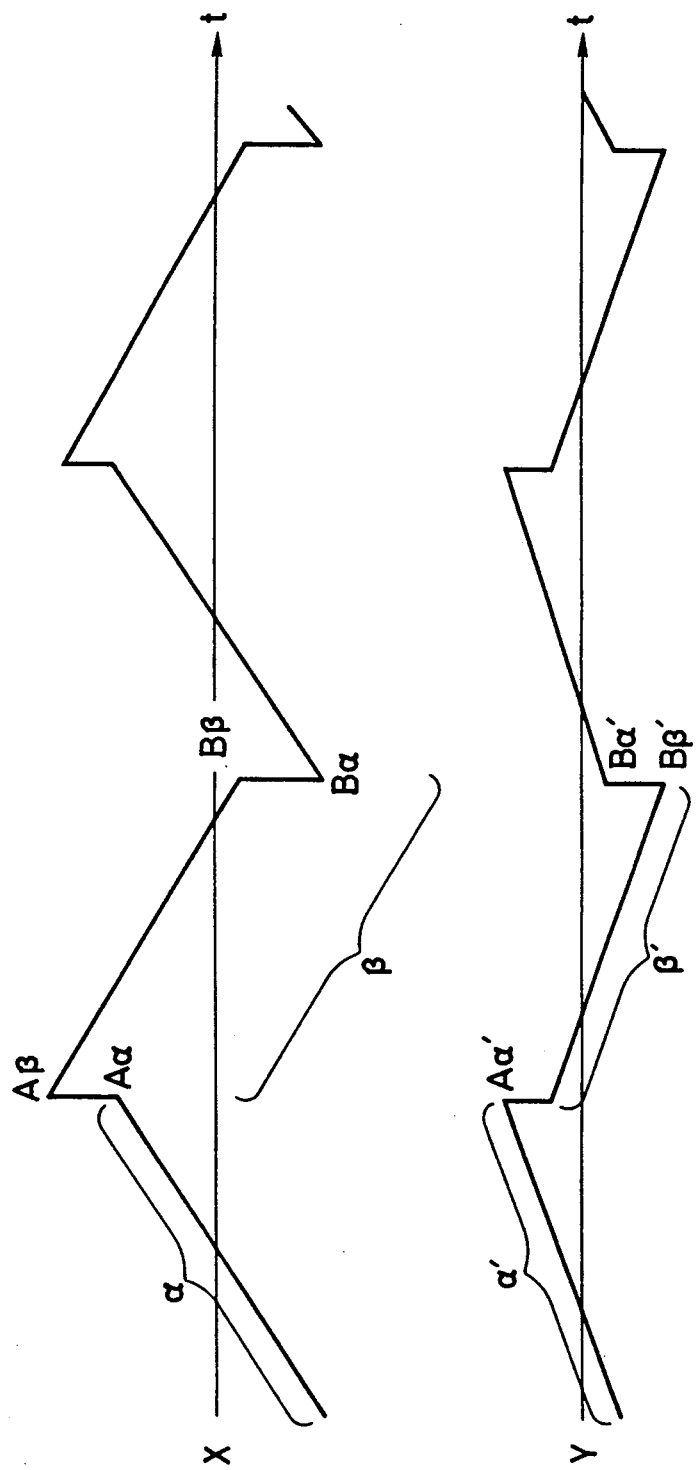

ION BEAM IRRADIATION APPARATUS

BACKGROUND OF THE INVENTION

This invention relates to an ion beam irradiation apparatus suitable for use in cancer radiotherapy.

Ion beam irradiation is widely employed for treating tumors, and in particular, tumors that are not easily accessible to surgery. The ion beam is produced by a particle accelerator, which is directed toward the tumor and controlled in so that the ions lodge in the tumor cells without damaging the surrounding tissue. The size of the tumor often exceeds the diameter of the beam. It is therefore necessary to spread the beam in such a way that the beam will deliver a substantially uniform ion dose to an area large enough to cover the entire tumor.

An efficient method of spreading an ion beam is to wobble the beam by a pair of deflection magnets, where one magnet deflects the beam in the x-direction and the other magnet deflects the beam in the y-direction. A prior-art apparatus employing this method has been used at the Bevalac facility at the Lawrence Berkeley Laboratory of the University of California. as described in *IEEE Transactions on Nuclear Science*, Vol. NS-32, No. 5, October 1985, and in *Medical Physics*, Vol. 14, No. 5, September/October 1987. The power supply of the prior-art apparatus, which includes a three-phase alternator and an autotransformer, supplies sinusoidal current waveforms offset by 90° C. in phase to the x- and y- deflection magnets. This apparatus causes the beam to be deflected in a circular path, and the radius of the beam may be adjusted by changing the amplitude of the waveforms. By having the beam trace three concentric circular paths it is possible to "paint" having a circular field 30 cm in diameter for example with a substantially uniform radiation distribution.

One problem with the prior-art apparatus is that tumors, particularly difficult tumors which require radiotherapy, are rarely circular in shape. The circular field must therefore be partially masked to avoid bombarding healthy tissue. However, a large percentage of the ions emitted from the accelerator is wasted and is increased when the circular field is partially masked the treatment time needed to achieve the required dose.

Another problem is that the circular field painted by the prior art apparatus is always centered on the beam axis. and cannot be moved. To irradiate different tumor sites it is therefore necessary to move the patient, a procedure which requires an unnecessary amount of time. The treatment time is an important factor in view of both patient discomfort and the high cost of the particle accelerator.

SUMMARY OF THE INVENTION

It is accordingly an object of the present invention to irradiate fields of a variety of shapes including both circular shapes and oblong racetrack shapes with a uniform ion dose.

Another object of this invention is to irradiate fields located at a distance from the ion beam axis.

An ion-beam irradiation apparatus according to this invention includes a particle accelerator for producing an ion beam, x-deflection magnets for deflecting the ion beam in the x-direction y-deflection magnets for deflecting the ion beam in the y-direction a first power supply for supplying exciting current having an ac component and a dc bias component to the x-deflection magnets, a second power supply for supplying exciting current having an ac component and a dc bias component to the y-deflection magnets and a control unit for controlling the amplitude and phase of the ac components and the sign and magnitude of the dc bias components.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 7 illustrates two sinusoidal waveforms with a dc bias;

FIGS. 9A to 9E illustrate the production of a triangular waveform with a dc bias added to the segments thereof;

FIGS. 10A to 10B illustrate two such waveforms with opposite dc biases added;

DETAILED DESCRIPTION OF THE EMBODIMENTS

A novel ion beam irradiation apparatus will be described below with reference to the drawings.

Figure 1:
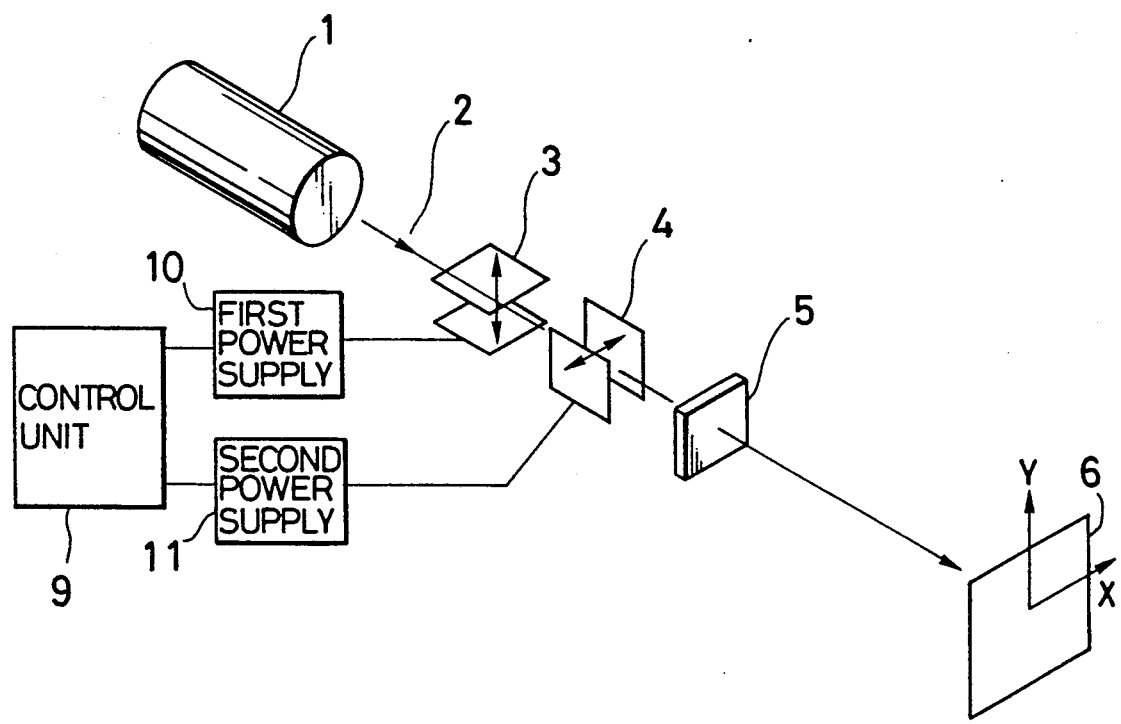
FIG. 1 is a schematic diagram illustrating the ion beam irradiation apparatus.

FIG. 1 illustrates the basic structure of the novel ion beam irradiation apparatus. The apparatus includes a particle accelerator 1 for accelerating ions to predetermined speeds, and generating a ion beam 2. A pair of x-deflection magnets 3 are disposed in the path of the ion beam 2 to deflect the beam in the x-direction, which is a direction perpendicular to the beam axis. A pair of y-deflection magnets 4 are disposed in the path of the ion beam 2 downstream of the x-deflection magnets 3 to deflect the beam in the y-direction, which is a direction perpendicular to both the beam axis and the x-direction. The x-deflection magnets 3 and the y-deflection magnets 4 are accordingly oriented at right angles to each other. A scatterer 5 is disposed in the path of the ion beam 2 downstream of the y-deflection magnets 4, to flatten the distribution of energy the ion beam 2. The beam is delivered to a target plane 6, which is located where the radiotherapy patient would be placed.

The deflection of the beam is controlled by a control unit 9 which sends control signals to first and second power supplies 10 and 11. The first power supply 10 supplies an exciting current, having an ac component and a dc bias component, to the x-deflection magnets 3.

The second power supply 11 supplies exciting current, having an ac component and a dc bias component to the pair of y-deflection magnets 4. The control signals from the control unit 9 control the amplitude and phase of the ac components, and the sign and magnitude of the dc bias components. The control unit 9 also sends control signals to the particle accelerator 1, which includes signals for controlling the intensity of the ion beam 2.

The general operation of the ion beam irradiation apparatus can be described as follows. The particle accelerator 1 produces an ion beam 2, which passes in turn between the x-deflection magnets 3 and the y-deflection magnets 4. The ion beam 2 is deflected in a direction perpendicular to the magnetic field generated by the x-deflection magnets 3 by an amount proportional to the strength of this magnetic field. Then, the beam is deflected in a direction perpendicular to the magnetic field generated by the y-deflection magnets 4 by an amount proportional to the strength of that magnetic field. Because the x-deflection magnets 3 and the y-deflection magnets 4 are oriented at right angles to each other, their magnetic fields are similarly oriented at right angles. Thereby the ion beam 2 can be deflected in both the x- and y-directions, so that the total deflection is equal to the vector sum of the independent deflections.

The strengths of the magnetic magnetic fields in the x-deflection magnets 3 and the y-deflection magnets 4 are varied under the control of the control unit 9. In this way the ion beam 2 can be steered to trace out a desired locus on the target plane 6. A novel feature of the present embodiment is that the locus can have a racetrack shape as will be illustrated later, and need not be centered on the beam axis.

The structure of the particle accelerator 1 the x- and y-deflection magnets 3 and 4, and the scatterer 5 is well known, and the control unit 9 may be a convental device such as a general-purpose computer. Detailed descriptions of these elements will be omitted. The first and second power supplies 10 and 11 are identical in structure and their circuit configuration will be described next.

Figure 2:
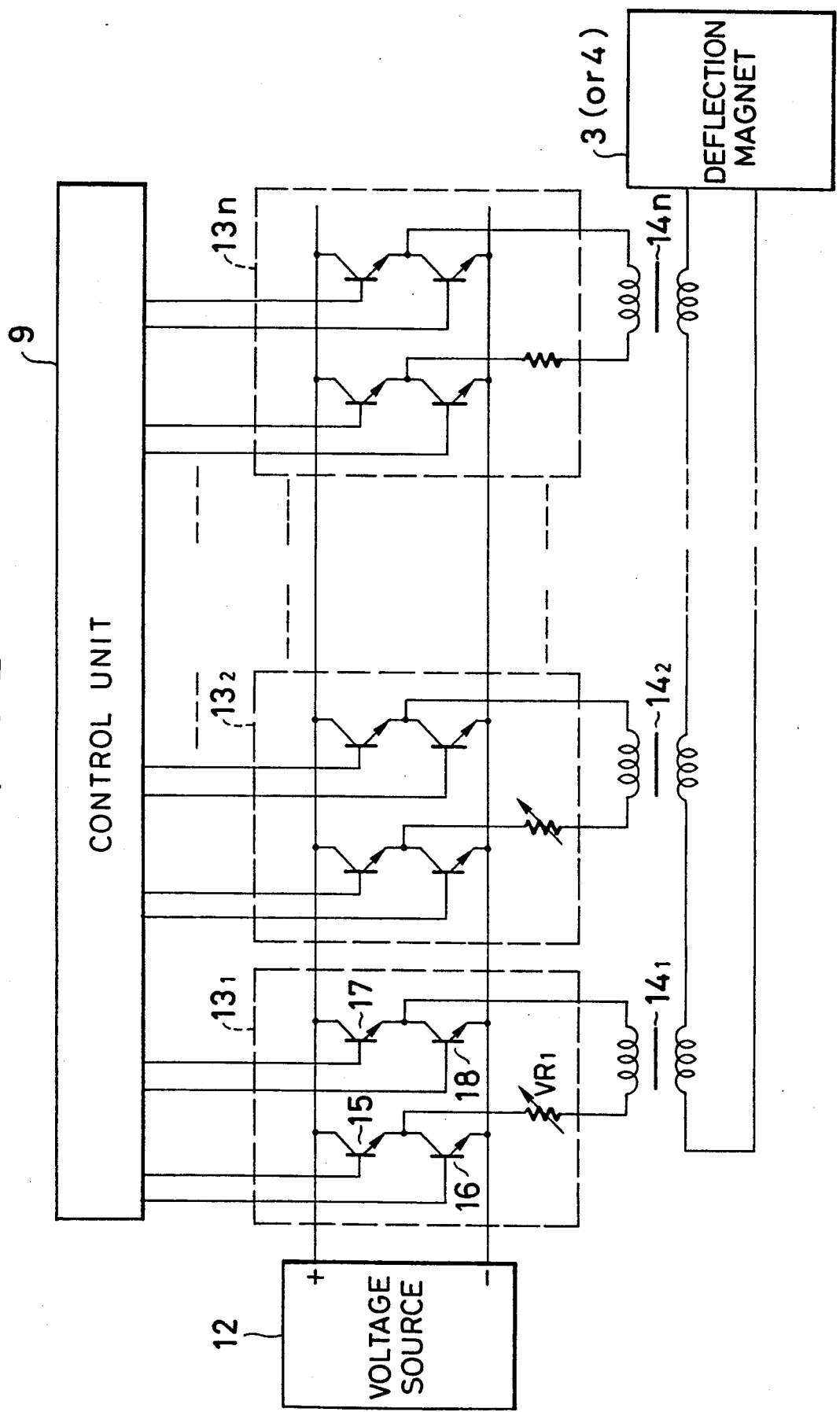
FIG. 2 is a circuit diagram of the power supplies in FIG. 1.

FIG. 2 is a circuit diagram of the first and second power supplies 10 and 11. Each power supply is a multiphase inverter-type power supply including a dc voltage source 12, inverter circuits $13_1$ to $13_n$, and coupling transformers $14_1$ to $14_n$ that are connected to respective inverter circuits $13_1$ to $13_n$. The coupling transformers $14_1$ to $14_n$ are connected in series to the x- or y-deflection magnets 3 or 4.

Each inverter circuit $13_1$ to $13_n$ includes four transistors 15, 16, 17, and 18 connected to form an inverter in the form of a single-phase bridge. The pair of transistors 15 and 16 are connected in series between the positive and negative terminals of the voltage source 12. The pair of transistors 17 and 18 are also connected in series between the positive and negative terminals of the voltage source 12, in parallel with the pair of transistors 15 and 16. In other words, the dc terminals of the inverter bridge are connected across the positive and negative terminals of the voltage source 12. The ac terminals of the inverter bridge, i.e., the node connecting the transistors 15 and 16, and the node connecting the transistors 17 and 18, are connected through a variable resistor $VR_1$ across the output terminals of the inverter circuit $13_1$. The first and second ends A and B of the primary winding of the coupling transformer $14_1$ are connected to the output terminals of the inverter circuit $13_1$.

The pair of transistors 15 and 18 are switched on and off simultaneously and the pair of transistors 10 and 17 are similarly switched on and off simultaneously. When the transistors 15 and 18 are on, the A end of the transformer $14_1$ is positive and the B end is negative, and when the transistors 16 and 17 are on, the A end is negative and the B end is positive. Thereby, switching the transistors 15, 16, 17, and 18 by the inverter circuit $13_1$ creates positive and negative voltage pulses in the primary winding of the coupling transformer $14_1$, which induces positive and negative current pulses in the secondary winding. The transistors in the inverter circuits $13_2$ to $13_n$ are likewise switched to create positive and negative pulses in the coupling transformers $14_2$ to $14_n$.

The base electrodes of the transistors 15, 16, 17, and 18 are connected to the control unit 9, which thus controls the switching of the transistors. The control unit 9 accordingly controls the timing of the pulses obtained from the coupling transformers $14_1$ to $14_n$, and selects whether each pulse is positive or negative.

The amplitude of the pulses obtained from the coupling transformers $14_1$ to $14_n$ depends on the voltage applied across their primary windings, which in turn depends on the resistance values of the variable resistors $VR_1$ and $VR_n$ in the inverter circuits $13_1$ to $13_n$. These resistance values are varied slightly from one inverter circuit to the next, so that pulses of different amplitudes can be obtained. This enables a variety of waveforms to be synthesized under the control of the control unit 9, as will be explained next.

The synthesis of a sinusoidal waveform, which can provide the ac component of the current supplied by the first or second power supply 10 or 11, will be described with reference to FIGS. 3 and 4. In these drawings the number of inverter circuits 13 and coupling transformers 14 is assumed to be 11 (n=11) and the resistance values of the variable resistors $VR_1$ to $VR_{11}$ are adjusted so that the amplitude of the pulses from the respective inverter circuits $13_1$ to $13_{11}$ varies gradually from a low value in the inverter circuit $13_1$ to a high value in the inverter circuit $13_6$, then back toward the low value in the inverter circuit $13_{11}$.

Figure 3:
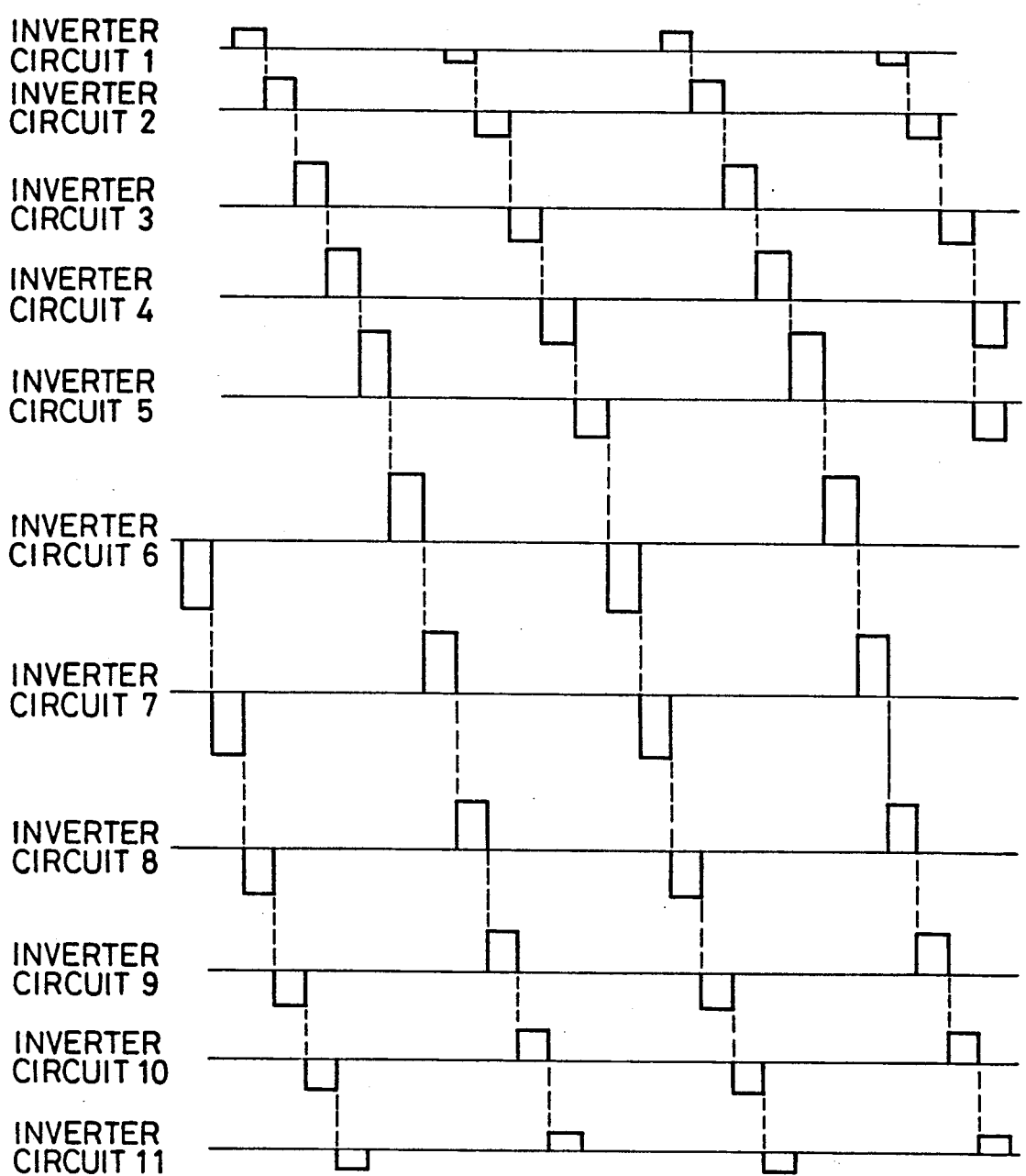
FIG. 3 is a timing chart illustrating a sequence of pulses produced by the power supply in FIG. 2.

FIG. 3 is a timing chart illustrating the pulses obtained from the inverter circuits $13_1$ to $14_n$. The inverter circuit $13_1$ is switched so as to obtain alternate positive and negative pulses. The inverter circuit $13_2$ is switched in the same way as the inverter circuit $13_1$ but the pulses of the inverter circuit 13, lag behind the pulses of the inverter circuit 13, by one pulse duration so that each positive or negative pulse from the inverter circuit $13_1$ is followed by a slightly larger pulse of the same sign from the inverter circuit $13_2$. Similarly, each of these pulses are followed by a slightly larger pulse of the same sign from the inverter circuit $13_3$ and this pattern continues on to the inverter circuit $13_6$. After the inverter circuit $13_6$, the sizes of the pulses gradually decrease in the inverter circuits $13_7$ through $13_{11}$.

Figure 4:
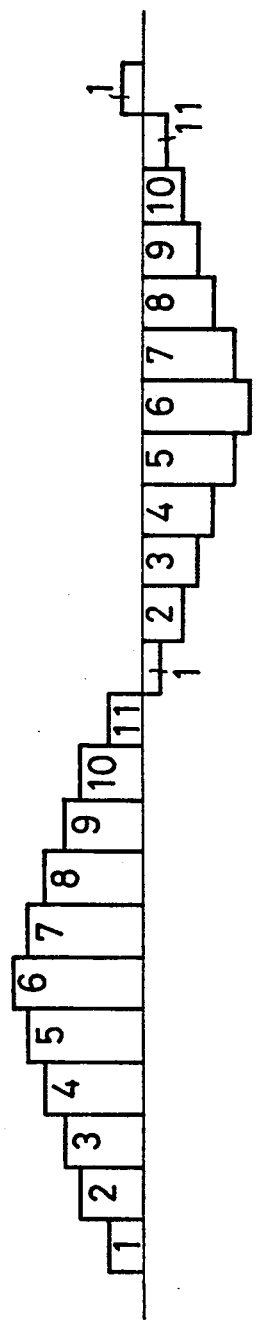
FIG. 4 illustrates how the pulses are assembled to approximate a sinusoidal waveform.

If the output waveforms of the inverter circuits $13_1$ to $13_{11}$ are combined, the waveforms approximate a sinusoidal waveform as illustrated in FIG. 4. The current pulses induced in the secondary windings of the coupling transformers $14_1$ to $14_{11}$ illustrate the same approximation to a sinusoidal waveform. Because the secondary windings of the coupling transformers $14_1$ to $14_{11}$ are connected in series, they supply this approximately sinusoidal waveform to the x- or y-deflection magnets 3 or 4.

Figure 5:
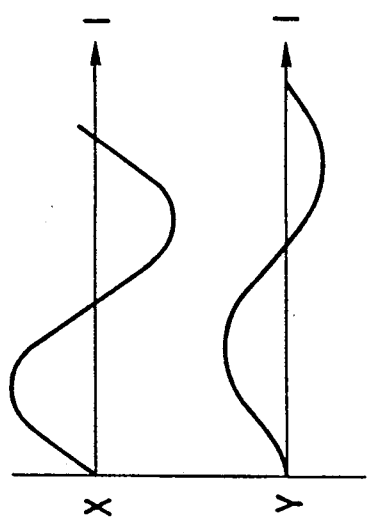
FIG. 5 illustrates two sinusoidal waveforms of arbitrary amplitude and phase relationship.

The sinusoidal currents supplied to the x-deflection magnets 3 and the y-deflection magnets 4 can be varied in both amplitude and phase as illustrated in FIG. 5, by providing a large enough number of inverter circuits having variable resistors with different resistance values and switching the circuits at appropriate times by the control signals from the control unit 9. If the sinusoidal current illustrated in the top line of FIG. 5 is supplied to the x deflection magnets 3 and the sinusoidal current illustrated in the bottom line of FIG. 5 is supplied to the y-deflection magnets 4, then the ion beam 2 will be deflected to as to trace out an elliptical path. If the two waveforms are equal in amplitude and offset by 90° in phase, the trace of the beam will be circular.

Figure 6:
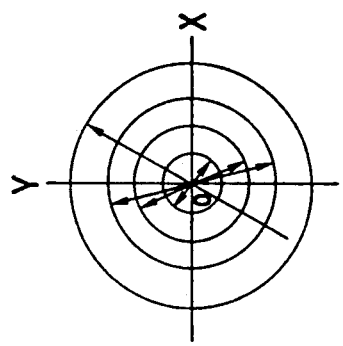
FIG. 6 illustrates the uniform irradiation of a circular field.

Circles of different diameters can be obtained by varying the amplitude of the sinusoidal waveforms. For example, the beam can be made to follow four concentric circular paths as illustrated in FIG. 6, with the circular paths centered at the beam axis. By suitably controlling the beam intensity, so that the intensity is lowest in the innermost circle and highest in the outermost circle, a substantially uniform irradiation of the entire circular field enclosed by the outermost circle will result, as in the prior art.

By suitably switching the inverter circuits $13_1$ to $13_n$, it is also possible to approximate waveforms with an arbitrary dc bias, such as the waveform illustrated in FIG. 7. For example, to produce the bottom waveform in FIG. 7, the inverter circuits $13_1$ to $13_n$ are switched so that the transistors 18 and 17 are always off and only the transistors 15 and 18 are switched on. Thereby, only positive pulses are produced.

Figure 8:
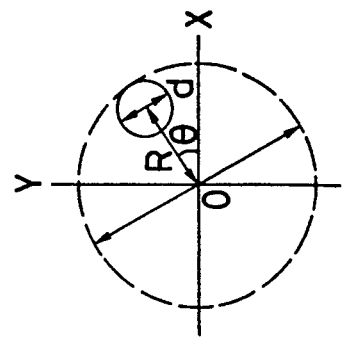
FIG. 8 illustrates the beam trace produced by the waveforms in FIG. 7.

FIG. 8 illustrates the result of the waveforms in FIG. 7. The beam traces a circular path, but the circle is offset from the beam axis O. The offset distance R and angle Θ can be varied by controlling the sizes of the two dc biases in FIG. 7. The diameter d of the circle can be varied by controlling the amplitude of the sinusoidal waveforms in FIG. 7.

Non-sinusoidal waveforms can also be approximated. For example, by switching just one of the inverter circuits $13_1$ to $13_n$ it is possible to supply a square wave to one of the coupling transformers $14_1$ to $14_n$ as illustrated in FIG. 9A. The current output obtained from the secondary winding of this coupling transformer is illustrated in FIG. 9B. Although the output waveform includes a series of nonlinear segments, the waveform is substantially linear for short intervals such as $t_1$ and $t_2$ at the beginning of each segment.

Accordingly it is possible to obtain a triangular output waveform by alternating a series of positive pulses that increases in magnitude with a series of negative pulses that increases in magnitude, as in FIG. 9C. FIG. 9C illustrates the waveform input to the primary windings of the coupling transformers $14_1$ to $14_n$. FIG. 9D illustrates the waveform output obtained from the secondary windings of the coupling transformers $14_1$ to $14_n$ and supplied as an ac component to the x- or y-deflection magnets 3 or 4. If this type of triangular waveform is supplied to both the x-deflection magnets 3 and the y-deflection magnets 4, the ion beam 2 will move back and forth in a straight line inclined at an angle that depends on the relative amplitude of the two triangular waves. The ability to generate a triangular waveform is a useful feature of this embodiment.

By slightly modifying the switching of the inverter circuits $13_1$ to $13_n$ it is possible to add dc biases to the segments of the triangular waveform in FIG. 9D, so that each segment may be shifted up or down. The ascending segments can be shifted in one direction by adding a dc bias of one polarity and the descending segments can be shifted in the opposite direction by adding a dc bias of the opposite polarity. Accordingly, waveforms similar to the waveform illustrated in FIG. 9E can be produced. In this example, the ascending segments are shifted up and the descending segments are shifted down. Such modified triangular waveforms can be used to obtain the racetrack irradiation pattern which is one of the novel features of an embodiment of the present invention, as will be explained next.

For a racetrack irradiation pattern, a pair of modified triangular waveforms having opposite dc biases are supplied to the x-deflection magnets 3 and the y-deflection magnets 4, as illustrated in FIGS 10A and 10B. In the waveform supplied to the x-deflection magnets 3 as illustrated in FIGS. 10A, negative dc bias is added to the ascending segments of the triangular waveform and a positive dc bias is added to the descending segments as illustrated in FIG. 10B while in the waveform supplied to the y-deflection magnets 4 positive dc bias is added to the ascending segments and a negative dc bias is added to the descending segments.

Figure 11:
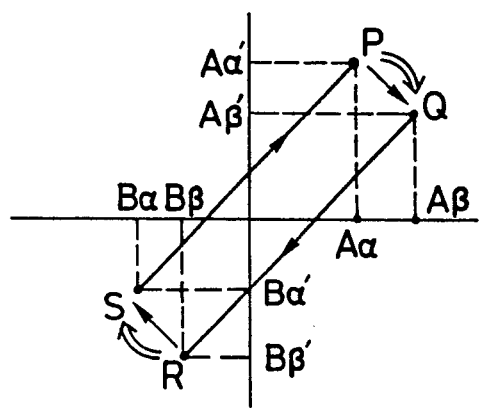
FIG. 11 illustrates the beam trace resulting from the waveforms in FIGS. 10A and 10B.

The trace of the ion beam 2 on the target plane 6 then becomes a pair of parallel lines as illustrated in FIG. 11. The values $A_\alpha$, $A_\beta$, $B_\alpha$, $B_\beta$, $A_\alpha'$, $A_\beta'$, $B_\alpha\alpha$, and $B_\beta'$ in FIGS. 10A and 10B correspond to the similarly labeled values in FIG. 11. The ascending segments of the waveforms, such as the segments labeled $\alpha$ and $\alpha'$ in FIGS. 10A and 10B, correspond to the segment SP in FIG. 11. The descending segments of the waveforms such as the segments labeled $\beta$ and $\beta'$ in FIGS. 10A and 10B, correspond to the segment QR in FIG. 11. The segments PQ and RS in FIG. 11 are transitional regions in which the current waveform does not change instantaneously from one value to another as illustrated in FIGS. 10A and 10B. The current waveform is actually somewhat rounded, which causes the beam to move along substantially the paths indicated by the arrows.

Figure 12:
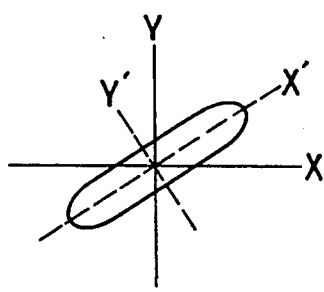
FIG. 12 illustrates a racetrack field uniformly irradiated by the waveforms in FIG. 11.

The field irradiated by the beam thus has the oblong racetrack shape illustrated in FIG. 12. The length and the inclination of the racetrack can be controlled by varying the amplitudes of the waveforms supplied to the x- and y-deflection magnets 3 and 4. For example, the x-dimension of the racetrack can be made larger by increasing $A_\alpha$ and $A_\beta$ FIGS. 10A and 10B, and by decreasing $B_\alpha$ and $B_\beta$. The spacing between the sides of the racetrack and the beam intensity can be adjusted by varying the differences, such as the difference between $A_\alpha$ and $A_\beta$ in FIGS. 10A and 10B. Suitable adjustments of this spacing enables a substantially uniform radiation dose to be delivered throughout the area encompassed by the racetrack; Thereby, tumors having an oblong shape can be treated in an efficient manner, by receiving substantially all of the ions produced from the particle accelerator 1.

Figure 13:
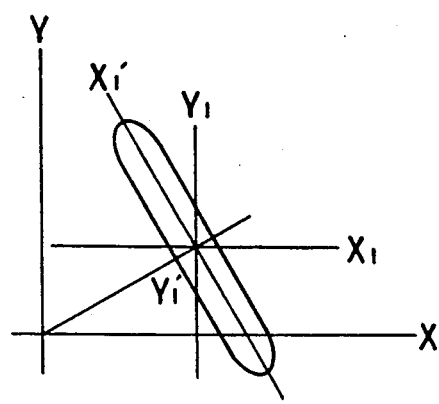
FIG. 13 illustrates a similar uniformly-irradiated racetrack field offset from the beam axis.

The racetrack need not be centered at the beam axis. By superimposing an overall dc has on the waveforms supplied to the x deflection magnets g and the pair of y-deflection magnets 4 it is possible to move the racetrack to a desired location away from the beam axis, as illustrated in FIG. 13. The underlying principle is the same as illustrated in FIGS. 7 and 8. Tumors of irregular shape can be treated by directing multiple racetrack patterns or other irradiation patterns such as the circular pattern in FIG. 8, at different parts of the tumor to provide complete coverage. As a result, substantially all of the ion beam can be delivered to the tumor area.

The novel ion beam irradiation apparatus can switch among different irradiation patterns such as the ones in FIGS. 6, 8, 12, and 13, at high speed. Therefore, a treatment session can be completed efficiently in a short time, without requiring the patient to be moved. Accordingly, single apparatus may be used to treat a larger number of patients, at a lower cost per patient, than in the prior art.

The scope of this invention is not limited to the embodiments illustrates in the drawings, and any modifications and variations that will be apparent to one skilled in the art may be included. For example, the inverter circuits need not have the variable resistors and the ac terminals of the inverter bridge in each inverter circuit may be connected directly to the output terminals of the inverter circuit. The voltages of the signals applied to the bases of the transistors may be varied so that the resistances of the transistors may be varied from one inverter circuit to another. This arrangement has the same effects as the inverter circuits having separate variable resistors. Also, the first and second power supplies 10 and 11 can be formed to produce more complex irradiation patterns than the circular and racetrack patterns illustrated in FIGS. 6, 8, 12 and 13. More generally the first and second power supplies can have any structure capable of producing current waveforms with ac components controllable in amplitude and phase, and dc bias components controllable in sign and magnitude.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An ion beam irradiation apparatus comprising:
   a particle accelerator for developing an ion beam;
   first deflection means disposed in the path of said ion beam, for deflecting said ion beam in a first direction perpendicular to the axis of the path of said ion beam;
   second deflection means disposed in the path of said ion beam, for deflecting said ion beam in a second direction perpendicular to the axis of the path of said ion beam and perpendicular to said first direction in which the path of said ion beam is deflected by said first deflection means;
   a first power supply for supplying a first exciting current having a first ac component and a first dc bias component to said first deflection means;
   a second power supply for supplying a second exciting current having a second ac component and a second dc bias component to said second deflection means; and
   control means for varying magnetic fields developed by said first and second deflection means in response to the amplitude and phase of said first and second ac components and the polarity and magnitude of said first and second dc bias components and thereby controlling the size and the direction scanned by said ion beam.

2. The ion-beam irradiation apparatus of claim 1, whereby said first and second ac components comprise triangular waveforms.

3. The ion-beam irradiation apparatus of claim 2, wherein a dc bias having a first polarity is added to the ascending segments of said triangular waveforms, and a dc bias having a second polarity opposite to said first polarity is added to the descending segments of said triangular waveforms.

4. The ion-beam irradiation apparatus of claim 3, wherein the triangular waveforms supplied to said first deflection means and said second deflection means have opposite dc biases.

5. The ion-beam irradiation apparatus of claim 1, wherein each of said first and second power supplies respectively comprise:
   a voltage source;
   a plurality of inverter circuits connected in parallel to said voltage source for receiving current from said voltage source and generating different voltages, the polarity of which can be switched under the control of said control means; and
   a plurality of coupling transformers corresponding to said plurality of inverter circuits, the primary windings of said transformers receive the voltages generated by said inverter circuits corresponding thereto and the secondary windings of said transformers are connected in series with each other.

6. The ion-beam irradiation apparatus of claim 5, wherein each of said plurality inverter circuits comprises a first pair of transistors connected in series between the position and negative terminals of said voltage source and a second pair of transistors connected in series between the positive and negative terminals of said voltage source in parallel with said first pair, one end of the primary winding of said coupling transformer corresponding to said inverter circuit being connected to a point disposed between said pair of transistors, the other end of the primary winding of said coupling transformer corresponding to said inverter circuit being connected to a point disposed between said second pair of transistors, and the base electrodes of said first and second pairs of transistors being connected to said control means.

7. The ion-beam irradiation apparatus of claim 5, wherein a plurality of resistors connect each of said plurality of inverter circuits to the primary winding of each of said plurality of coupling transformers, said plurality of resistors being set so that the amplitude of the different voltages generated from said plurality of inverter circuits vary gradually from a low value to a high value and back to said low value.

8. A method for irradiating an ion beam, comprising the steps of:
   (a) developing an ion beam;
   (b) developing a first exciting current having a first ac component and a first dc bias component;
   (c) deflecting the path of said ion beam in a first direction perpendicular to the axis of the path of said ion beam in response to said step (b);
   (d) developing a second exciting current having a second ac component and a second dc bias component;
   (e) deflecting the path of said ion beam in a second direction perpendicular to the axis of the path of said ion beam and perpendicular to said first direction in which the path of said ion beam is deflected at said step (c) in response to said step (d); and
   (f) varying magnetic fields developed at said steps (c) and (e) for deflecting the path of said ion beam in response to the amplitude and phase of said first and second ac components and the polarity and magnitude of said first and second dc bias components and thereby controlling the size and the direction scanned by said ion beam.

* * * * *